United States Patent
Michal et al.

(10) Patent No.: US 9,533,127 B2
(45) Date of Patent: Jan. 3, 2017

(54) METHODS FOR INHIBITING REPERFUSION INJURY

(75) Inventors: Eugene T. Michal, San Francisco, CA (US); Peter L. Callas, Castro Valley, CA (US); Florian N. Ludwig, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 2005 days.

(21) Appl. No.: 11/492,388

(22) Filed: Jul. 24, 2006

(65) Prior Publication Data

US 2008/0017202 A1    Jan. 24, 2008

(51) Int. Cl.
*A61M 31/00*    (2006.01)
*A61M 25/10*    (2013.01)

(52) U.S. Cl.
CPC .... *A61M 25/104* (2013.01); *A61M 2025/1095* (2013.01)

(58) Field of Classification Search
CPC .................. A61M 2025/1095; A61M 25/104; A61M 2025/1097
(Continued)

(56) References Cited

U.S. PATENT DOCUMENTS

| 4,142,530 A | 3/1979 | Wittkampf |
| 4,343,433 A | 8/1982 | Sickles |

(Continued)

FOREIGN PATENT DOCUMENTS

| WO | WO-9749484 | 12/1997 |
| WO | WO-9856894 | 12/1998 |

(Continued)

OTHER PUBLICATIONS

Saeed, Rubina W. et al., "Ascorbic Acid Blocks the Growth Inhibitory Effect of Tumor Necrosis Factor-alpha on Endothelial Cells," Experimental Biology and Medicine 228:855-865, 2003.

(Continued)

*Primary Examiner* — Gregory Anderson
*Assistant Examiner* — Christina Lauer
(74) *Attorney, Agent, or Firm* — Blakely, Sokoloff, Taylor & Zafman; Stacie J. Sundquist; William Thomas Babbitt

(57) ABSTRACT

A method that includes introducing a catheter assembly to an obstructed region of a blood vessel lumen and recanalizing the obstructed region with the catheter assembly is disclosed. Prior to or during recanalization, a treatment agent may be delivered through the catheter assembly to a vessel region downstream to the obstructed region. The treatment agent may have a property that will inhibit reperfusion injury. Alternatively, a medical device may be introduced to an obstructed region of a blood vessel lumen and the obstructed region recanalized with the medical device. The treatment agent may be delivered to a vessel region downstream to the obstructed region. The treatment agent may include at least one of an immunosuppresant and an antioxidant. In other methods, a delivery cannula may be introduced to an unperfused region of an occluded vessel without disrupting the occlusion and the treatment agent having a property that will inhibit reperfusion injury may be delivered to the unperfused region through the delivery cannula. After delivering the treatment agent, the occluded vessel may be recanalized by advancing an angioplasty device into the occluded vessel.

34 Claims, 6 Drawing Sheets

(58) Field of Classification Search
USPC ... 604/500, 501, 506, 21; 424/432; 600/500, 600/501, 506, 21
See application file for complete search history.

(56) References Cited

U.S. PATENT DOCUMENTS

| | | | |
|---|---|---|---|
| 4,813,934 A | | 3/1989 | Engelson et al. |
| 4,873,978 A | * | 10/1989 | Ginsburg ............... 606/198 |
| 4,956,128 A | | 9/1990 | Hommel et al. |
| 4,981,625 A | | 1/1991 | Rhim et al. |
| 5,071,649 A | * | 12/1991 | Hunter ............... 424/78.38 |
| 5,137,513 A | * | 8/1992 | McInnes et al. ......... 604/103.05 |
| 5,158,548 A | | 10/1992 | Lau et al. |
| 5,159,937 A | | 11/1992 | Tremulis |
| 5,273,052 A | | 12/1993 | Kraus et al. |
| 5,648,331 A | | 7/1997 | Koudsi et al. |
| 5,653,689 A | | 8/1997 | Buelna et al. |
| 5,759,937 A | | 6/1998 | Hovis et al. |
| 5,797,876 A | | 8/1998 | Spears et al. |
| 5,925,016 A | | 7/1999 | Chornenky et al. |
| 5,935,122 A | | 8/1999 | Fourkas et al. |
| 6,022,336 A | | 2/2000 | Zadno-Azizi et al. |
| 6,022,363 A | | 2/2000 | Walker et al. |
| 6,044,845 A | * | 4/2000 | Lewis ............... 128/898 |
| 6,066,152 A | | 5/2000 | Strauss et al. |
| 6,093,557 A | | 7/2000 | Pui et al. |
| 6,179,871 B1 | | 1/2001 | Halpern |
| 6,193,686 B1 | * | 2/2001 | Estrada ............... A61M 25/09 604/103.09 |
| 6,231,588 B1 | | 5/2001 | Zadno-Azizi |
| 6,235,007 B1 | | 5/2001 | Divino, Jr. et al. |
| 6,309,379 B1 | | 10/2001 | Willard et al. |
| 6,387,324 B1 | | 5/2002 | Patterson et al. |
| 6,435,189 B1 | | 8/2002 | Lewis et al. |
| 6,436,087 B1 | | 8/2002 | Lewis et al. |
| 6,481,439 B1 | | 11/2002 | Lewis et al. |
| 6,494,862 B1 | * | 12/2002 | Ray et al. ............... 604/96.01 |
| 6,596,235 B2 | | 7/2003 | Divino, Jr. et al. |
| 6,599,283 B1 | | 7/2003 | Marzilli et al. |
| 6,660,034 B1 | | 12/2003 | Mandrusov et al. |
| 6,666,880 B1 | | 12/2003 | Chiu et al. |
| 6,783,541 B2 | | 8/2004 | Stephens et al. |
| 6,905,476 B2 | | 6/2005 | Ponzi |
| 7,008,411 B1 | * | 3/2006 | Mandrusov et al. ......... 604/506 |
| 7,326,195 B2 | | 2/2008 | Willard et al. |
| 7,371,248 B2 | | 5/2008 | Dapolito et al. |
| 7,837,650 B1 | | 11/2010 | Cox et al. |
| 8,521,259 B2 | * | 8/2013 | Mandrusov et al. ......... 600/427 |
| 2001/0049517 A1 | * | 12/2001 | Zadno-Azizi ............ A61B 17/22 604/509 |
| 2002/0081732 A1 | | 6/2002 | Bowlin et al. |
| 2002/0132845 A1 | | 9/2002 | Miller et al. |
| 2002/0151866 A1 | * | 10/2002 | Lundkvist et al. ............ 604/506 |
| 2002/0169436 A1 | | 11/2002 | Gurn et al. |
| 2003/0022870 A1 | | 1/2003 | Dzau et al. |
| 2004/0021017 A1 | | 2/2004 | Sumiyoshi et al. |
| 2004/0058887 A1 | | 3/2004 | Bowlin et al. |
| 2004/0087464 A1 | | 5/2004 | Stoessel et al. |
| 2004/0142014 A1 | * | 7/2004 | Litvack et al. ............... 424/423 |
| 2004/0167467 A1 | | 8/2004 | Harrison et al. |
| 2005/0015048 A1 | | 1/2005 | Chiu et al. |
| 2005/0107741 A1 | | 5/2005 | Willard et al. |
| 2005/0249775 A1 | | 11/2005 | Falotico et al. |
| 2006/0051407 A1 | * | 3/2006 | Richter et al. ............... 424/450 |
| 2006/0265043 A1 | * | 11/2006 | Mandrusov et al. ......... 623/1.11 |
| 2007/0208297 A1 | | 9/2007 | Ainsworth et al. |
| 2007/0218118 A1 | | 9/2007 | Michal et al. |

FOREIGN PATENT DOCUMENTS

| | | |
|---|---|---|
| WO | WO-02076424 | 10/2002 |
| WO | WO-03059266 | 7/2003 |
| WO | WO-2007012947 | 2/2007 |

OTHER PUBLICATIONS

Chamoun, Fady et al., "Pathophysiologic Role of Selectins and their Ligands in Ischemia Reperfusion Injury," Frontiers in Bioscience 5, Nov. 1, 2000, pp. 103-109.

Danon D. et al., "Surface charge and flow properties of endothelial membranes in aging rats," Mech Ageing Dev, Sep.-Oct. 1980; 14(1-2):145-53.

Bartlett, Robert L., "Leukocyte Mediated Reperfusion Injury: What Role HBO?" http://www.richmond-hyperbaric.com/PHHC.studies.Reperfusion.htm.

Skyschally, Andreas et al., "Coronary microembolization," Basic Research in Cardiology vol. 101, Aug. 2006, pp. 373-382.

Abbott Cardiovascular Systems Inc., PCT Search Report and Written Opinion mailed May 2, 2008, PCT Application No. PCT/US2007/016432, 18 pages.

Kim, G., "Production of microsized PMMA droplets using electrospraying with various auxiliary fields", Journal of Colloid and Interface Science, 299, (2006), pp. 593-598.

Rietveld, I. B. et al., "Production of Polymer Films with Electrospray", Proceeding of the 8th Polymers for Advanced Technologies International Symposium, Budapest, Hungary, (Sep. 13-16, 2005).

"What is Electrospray?", New Objective, Inc., (2004) <http://www.newobjective.com/electrospray>.

Abbott Cardiovascular Systems, IPRP mailed Jan. 22, 2009 for PCT/US2007/013315.

Abbott Cardiovascular Systems, PCT Search Report and Written Opinion dated Mar. 4, 2008 for PCT/US2007/013315.

Abbott Cardiovascular Systems, Non final office action mailed May 20, 2010 for U.S. Appl. No. 11/485,934.

Abbott Cardiovascular Systems, Final office action mailed Oct. 27, 2010 for U.S. Appl. No. 11/485,934.

Abbott Cardiovascular Systems, Non-Final Office Action mailed Mar. 30, 2011 for U.S. Appl. No. 11/485,934.

Abbott Cardiovascular Systems, Non-Final Office Action mailed Jan. 28, 2013 for U.S. Appl. No. 11/485,934.

Abbott Cardiovascular Systems, Final Office Action mailed Oct. 18, 2011 for U.S. Appl. No. 11/485,934.

Abbott Cardiovascular Systems, Non Final Office Action dated Jun. 11, 2009 for U.S. Appl. No. 11/026,598.

Abbott Cardiovascular Systems, Final office action dated Oct. 16, 2009 for U.S. Appl. No. 11/026,598.

Abbott Cardiovascular Systems, Non final office action dated Mar. 30, 2010 for U.S. Appl. No. 11/026,598.

Abbott Cardiovascular Systems, Non-final Office Action mailed Aug. 4, 2011 for U.S. Appl. No. 12/943,879.

Abbott Cardiovascular Systems, Final Office Action mailed Feb. 2, 2012 for U.S. Appl. No. 12/943,879.

Abbott Cardiovascular Systems, Non-Final Office Action dated Dec. 5, 2012 for U.S. Appl. No. 13/571,110.

Assmus, B., et al., "Transplantation of Progenitor Cells and Regeneration Enhancement in Acute Myocardial Infarction (TOPCARE-AMI)", Clinical Investigation and Reports, Circulation, 106, (2002), 3009-3017.

Mandrusov, E., et al., "Membrane-based Cell Affinity Chromatography to Retrieve Viable Cells, Biotechnol", Prob. 1995, 11, 208-213, Artificial Organs Research Laboratory, Department of Chemical Engineering, Material Science and Metallurgy, Columbia University, New York, New York 10027, and Louisville, Kentucky 40292.

Abbott Cardiovascular Systems, Non-Final Office Action mailed Sep. 10, 2015, U.S. Appl. No. 14/299,764.

* cited by examiner

METHODS FOR INHIBITING REPERFUSION INJURY

FIELD

Methods for inhibiting reperfusion injury.

BACKGROUND

A major component of morbidity and mortality attributable to cardiovascular disease occurs as a consequence of the partial or complete blockage of vessels carrying blood in the coronary and/or peripheral vasculature. When such vessels are partially occluded, lack of blood flow causes ischemia to the capillary beds and muscle tissues supplied by such vessel, consequently inhibiting muscle contraction and proper function. Total occlusion of blood flow causes necrosis of the muscle tissue.

Blood vessel occlusions are commonly treated by mechanically enhancing blood flow in the affected vessels. Such mechanical enhancements are often provided by employing surgical techniques that attach natural or synthetic conduits proximal and distal to the areas of occlusion, thereby providing bypass grafts, or revascularization by various means to physically enlarge the vascular lumen at the site of occlusion. These revascularization procedures involve such devices as balloons, endovascular knives (atherectomy), and endovascular drills. The surgical approach is accompanied by significant morbidity and even mortality, while the angioplasty-type processes are complicated by recurrent stenoses in many cases.

Additional complications arise due to the restoration of blood flow to the ischemic tissues. This phenomenon is commonly referred to as reperfusion injury and may be more damaging to the tissue than ischemia. In particular, the absence of oxygen and nutrients typically delivered to the ischemic tissue region by the blood creates a condition in which the restoration of circulation results in inflammation and oxidative damage rather than restoration of normal function. Thus, tissue damage attributed to reperfusion injury is primarily caused by the inflammatory response of the damaged tissue. In particular, in response to the tissue damage, white blood cells carried to the region by the reintroduced blood supply produce inflammatory factors including cytokines such as interleukins and free radicals. This new supply of oxygen forms within cells which may damage cellular proteins, DNA and the plasma membrane. This may in turn cause the release of additional free radicals resulting in further cellular damage. The cytokines activate and guide leukocytes to the injured tissue causing microcirculation "white" clots and further release of free radicals and toxic substances. In some individuals, reperfusion injury may be lower than in others due to the natural antioxidant load or inflammatory responses of the individual. In general, however, this reperfusion mediated injury may cause more damage then ischemia alone.

SUMMARY

According to the present invention, methods for inhibiting reperfusion injury are described. In one embodiment, the method representatively includes introducing a catheter assembly to an obstructed region of a blood vessel lumen. The method further includes recanalizing the obstructed region with the catheter assembly and prior to or during recanalization, delivering a treatment agent through the catheter assembly to a vessel region downstream to the obstructed region. The treatment agent has a property that will inhibit reperfusion injury. In one embodiment, the treatment agent is an immunosuppressant and/or an antioxidant. As used herein, treatment agents are intended to include, but are not intended to be limited to, drugs, biologically active agents, chemically active agents, therapeutic agents, and the like, and pharmaceutical compositions thereof, which can be used to deliver a treatment agent to a treatment site as described herein.

According to another embodiment, a method is described that includes introducing a medical device to an obstructed region of a blood vessel lumen. The obstructed region is recanalized with the medical device. A treatment agent may then be delivered to a vessel region downstream to the obstructed region. The treatment agent may include at least one of an immunosuppressant and an antioxidant. The medical device may be an angioplasty catheter or a stent delivery catheter.

According to another embodiment, a method is described including introducing a delivery cannula to an unperfused region of an occluded vessel without disrupting the occlusion. A treatment agent may be delivered through the delivery cannula to an unperfused region of the occluded vessel. After delivering the treatment agent, the occluded vessel may be recanalized by advancing an angioplasty device into the occluded vessel.

In some embodiments, the treatment agent may be an immunosuppressant including, but not limited to, corticosteroids, everolimus, rapamycin, and derivatives thereof. The treatment agent may further be an antioxidant including but not limited to ascorbic acid, proanthocyanadins, carotenoids, tocopherol, selenium, N-acetyl-carnitine, R-lipoic acid and coenzyme Q-10. Still further, the treatment agent may be a drug including, but not limited to, cariporide, eniporide, zoniporide, nicaraven, MLN01, nicorandil, raloxifene, edaravone, Adenoscan® and carvedilol.

BRIEF DESCRIPTION OF THE DRAWINGS

The features of the described embodiments are specifically set forth in the appended claims. However, the embodiments are best understood by referring to the following description and accompanying drawings, in which similar parts are identified by like reference numerals.

DETAILED DESCRIPTION

Methods for inhibiting reperfusion injury are disclosed herein. Such methods may be particularly effective in treating acute myocardial infarction (AMI), reducing myocardial infarct size and as a prophylactic treatment for microembolization caused by plaque rupture during routine angioplasty or stenting in non-AMI patients. Reducing reperfusion injury further reduces border zone apoptosis and resultant infarct expansion. A smaller infarct zone reduces the chance that patients will progress to hypertrophied failing.

Figure 1:
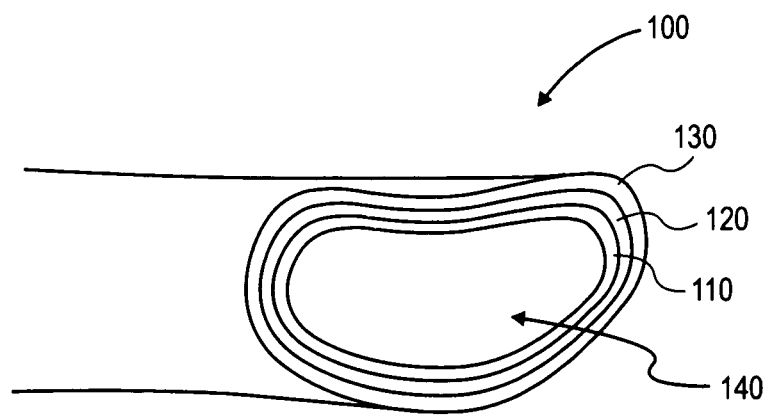
FIG. 1 shows a schematic side and sectional view of a blood vessel.

Referring to FIG. 1, a non-diseased artery is illustrated as a representative blood vessel. Blood vessel 100 includes an arterial wall having a number of layers. Inner most layer 110 is generally referred as to the intimal layer that includes the endothelium, the subendothelial layer, and the internal elastic lamina. Medial layer 120 is concentrically outward from inner most layer 110 and bounded by external elastic lamina. There is no external elastic lamina in a vein. Medial layer 120 (in either an artery or vein) primarily consists of smooth muscle fibers and collagen. Adventitial layer 130 is concentrically outward from medial layer 120. The arterial wall (including inner most layer 110, medial layer 120 and adventitial layer 130 defines lumen 140 of blood vessel 100.

Figure 2:
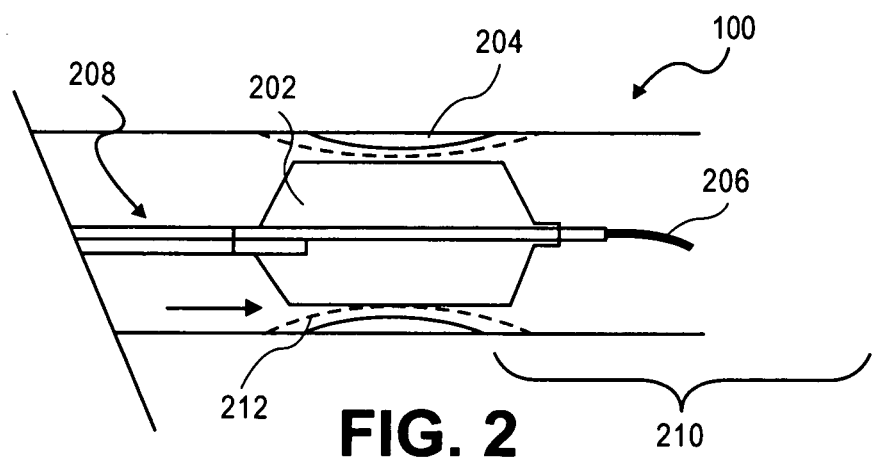
FIG. 2 shows a cross-sectional side view of a distal portion of a catheter assembly in a blood vessel during an angioplasty procedure.

Stenosis or occlusion of a blood vessel such as blood vessel 100 occurs by the build-up of plaque on inner most layer 110. The stenosis or occlusion can result in decreased blood flow through lumen 140. One technique to address this is angioplasty. FIG. 2 shows a portion of an artery of blood vessel 100 including stenosis or occlusion 204. As a result of the occlusion, blood flow to region 210 distal to occlusion 204, hereinafter referred to as a treatment region, is reduced and in some cases completely stopped by occlusion 204. Accordingly, treatment region 210 is susceptible to reperfusion injury once the occluded region is recanalized. FIG. 2 generally illustrates recanalization of vessel 100 using a catheter assembly 208 including balloon 202. In this aspect, balloon 202 may be advanced over guidewire 206 to occlusion 204. Balloon 202 may be briefly inflated one or more times to dilate the vessel and/or minimize the size of the stenosis or occlusion. In one embodiment, a stent 212 may be placed over balloon 202 to assist in maintenance of the shape of the vessel lumen. FIG. 2 shows balloon 202 in an expanded state contacting and exerting pressure on occlusion 204. The dilating of a vessel or minimizing of a stenosis or occlusion may restore blood flow in blood vessel 100 to levels approaching those prior to the formation of the stenosis or occlusion.

Figure 3:
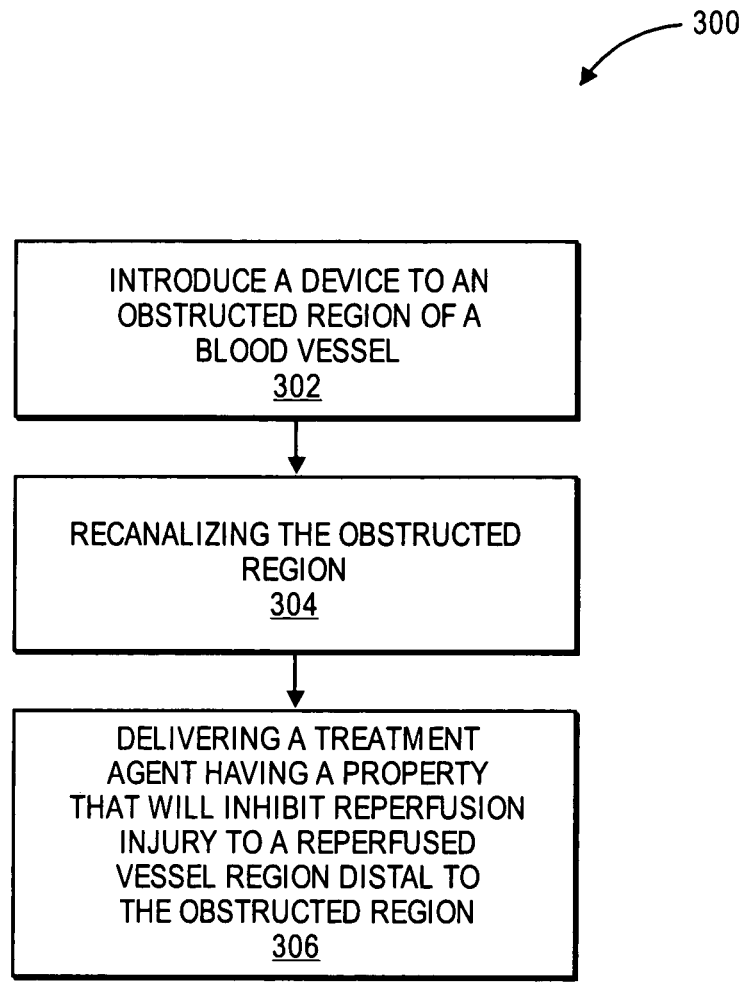
FIG. 3 illustrates a flow chart of a method for delivering a treatment agent to a reperfused region of a blood vessel.

As previously discussed, injury due to reperfusion of the ischemic vessel region may be greater than injury due to ischemia alone. In this aspect, it may be desirable to deliver a treatment agent to the ischemic region prior to or during recanalization to reduce and/or inhibit reperfusion injury within the region. As used herein, the ischemic vessel region is a region of vessel and/or tissue downstream or distal to an occluded region relative to blood flow. FIG. 3 illustrates a flow chart of a method for delivering a treatment agent to a reperfused region of a blood vessel. In this aspect, a delivery device is introduced to an obstructed region of a blood vessel (block 302). The blood vessel may be recanalized (block 304) according to the method generally discussed above and as will be discussed in further detail below. Upon recanalization, a treatment agent having a property that will inhibit reperfusion injury may be delivered to the reperfused region distal to or downstream from the obstructed region (block 306). Alternatively, a delivery cannula may be introduced to an unperfused region of the occluded vessel without disrupting the occlusion. In this aspect, the treatment agent is delivered through the delivery cannula prior to recanalizing the occluded vessel to pretreat the ischemic region prior to reperfusing the region.

A. Treatment Agents

The inflammatory injury cascade and oxidative species released during the reperfusion period are key components leading to reperfusion injury. Thus, treatment agents may include agents having a property to inhibit inflammatory pathways occurring during reperfusion such as immunosuppressants. One exemplary pathway may be that leading to the expression of TNF-alpha. TNF-alpha has a pro-apoptotic effect on endothelial cells. Accordingly, by reducing the expression of TNF-alpha, an inflammatory response triggered by ischemia may be reduced thereby further reducing the occurrence of a reperfusion injury at the reperfused vessel region. Representative immunosuppressants may include, but are not limited to, corticosteroids, everolimus, rapamycin, and/or derivatives thereof.

Alternatively, treatment agents may include an agent which curbs or inhibits the effects of oxidative species released at a site of injury. Such agents may include antioxidants. Representative antioxidants may include, but are not limited to, ascorbic acid, proanthocyanadins, carotenoids, tocopherol, selenium, N-acetyl-carnitine, R-lipoic acid and coenzyme Q-10 (Co Q10).

Still further, the treatment agent may be a drug having a Na+/H+ channel inhibiting property. During the early stages of cardiac ischemia, a sarcolemmal protein known as the Na+/H+ exchanger is activated and produces a large influx of Na+. The accumulated intracellular Na+ is in turn exchanged for Ca2+. This intracellular Na+ and Ca2+ overload during ischemia and reperfusion, in turn, is linked to the development of myocardial arrhythmia, contractile dysfunction, and cell death. Thus, inhibiting the Na+/H+ exchanger (i.e. Na+/H+ channel) may reduce cellular damage caused during reperfusion. Representative channel inhibitors may include, but are not limited to, cariporide, eniporide and zoniporide.

Alternatively, the drug may be an estrogen receptor antagonist. Estrogen receptor antagonists are believed to, in addition to preventing osteoporosis in postmenopausal women, have estrogen agonist effects on cardiovascular disease. Representative estrogen receptor agonists may include, but are not limited to, raloxifene.

Other representative drugs may include free radical scavengers including, but not limited to, nicaraven, and edaravone, beta blockers and/or antioxidants including, but not limited to, carvedilol. Alternatively, the drug may be, but is not limited to, an adenosine infusion such as Adenoscan®, an adenosine A1/A2 agonist such as AMP-579, a platelet activating factor-acetylhydrolase such as rPAF-AH and/or MLN01, formerly LDP-01, Anti-CD11/CD18 mAb.

In one embodiment, a single treatment agent may be delivered to the desired vessel region. Alternatively, the treatment agent delivered to the desired vessel region may be a combination of any number of the above-described immunosuppressants, antioxidants and/or drugs. For example, in one embodiment, the treatment agent may be an immunosuppressant such as a corticosteroid and an antioxidant such as ascorbic acid. Alternatively, the treatment agent may be any of the above described immunosuppressants in combination with a drug.

The treatment agent may be delivered to a target region in the form of, for example, a solution. The solution may include the treatment agent combined with any substance suitable for facilitating delivery of the treatment agent to the target region, for example a buffer. The amount of each agent in solution may be any amount sufficient to have an inhibitory effect on reperfusion injury. In one embodiment, the amount of each agent may be anywhere from zero to 100 percent weight by volume (w/v).

B. Carriers

In one embodiment, the treatment agent may be packaged or encapsulated in a carrier. A carrier may include a matrix that contains one or more treatment agents. A suitable carrier may take the form of a nanoparticle (e.g., nanosphere), microparticle (e.g., microsphere), liposome, and the like particles, as the situation may dictate. For example, the carrier may be a liposome or other outer shell such as, for example, lipid or polymer membranes, polymer shells, or other lipid-philic shells. In one embodiment, a surface of the carrier may be modified to enhance retention of the carrier and encapsulated treatment agent at the desired region.

In one aspect, the carrier may be a sustained-release carrier. The sustained-release carrier including a treatment agent may be strategically placed, for example, within an unperfused or reperfused region of a vessel distal to an occlusion to inhibit reperfusion injury at the selected location. Suitable materials for sustained-release carriers may include, but are not limited to, encapsulation polymers such as poly (L-lactide), poly (D,L-lactide), poly (glycolide), poly (lactide-co-glycolide), polycaprolactone, polyanhydride, polydiaxanone, polyorthoester, polyamino acids, or poly (trimethylene carbonate), and combinations thereof.

The carrier may provide for release of the treatment agent for a period of time sufficient to reduce reperfusion injury but not so long so as to prevent normal healing and scar formation necessary to prevent ventricular aneurism. In one embodiment, sustained release of the treatment agent occurs within a period of up to three days. In another embodiment, sustained release of the treatment agent occurs within a period of from one to three days. Representatively, in one embodiment, 100 percent of the drug is released over a 72 hour period. It is further contemplated that sustained release microparticle formulations with different release rates may be delivered in combination to achieve multi-modal release profiles over a period of time.

To form a sustained-release carrier composition of, for example, microparticles or nanoparticles (e.g., microspheres or nanospheres) or liposomes comprising one or more treatment agents and/or a modified carrier surface, the following techniques may be used.

1. Solvent Evaporation

In this method, the polymer is dissolved in a volatile organic solvent such as methylene chloride. The treatment agent is then added to the polymer solution either as an aqueous solution containing an emulsifying agent such as polyvinyl alcohol (PVA), or as a solid dispersion, and stirred, homogenized or sonicated to create a primary emulsion of protein in the polymer phase. This emulsion is stirred with an aqueous solution containing an emulsifying agent such as PVA to create a secondary emulsion of treatment agent containing polymer in the aqueous phase. This emulsion is stirred in excess water, optionally under vacuum to remove the organic solvent and harden the particles. The hardened particles are collected by filtration or centrifugation and lyophillized. A desired particle size (e.g., microparticle or nanoparticle) is selected by varying the preparation conditions (e.g., viscosity of the primary emulsion, concentration of the treatment agent, mixing (shear) rate, etc.). The particles tend to adopt a spherical shape in response to minimizing surface tension effects.

2. Coacervation:

In this method, a primary emulsion of treatment agent in an aqueous phase is formed as in the solvent evaporation method. This emulsion is then stirred with a non-solvent for the polymer, such as silicone oil to extract the organic solvent and form embryonic particles of polymer with trapped treatment agent. The non-solvent is then removed by the addition of a volatile second non-solvent such as heptane, and the particles hardened. The hardened particles are collected by filtration or centrifugation and lyophilized. Again, the particle size is selected as described above with reference to solvent evaporation.

3. Spray Drying:

In this method, a treatment agent, formulated as lyophilized powder is suspended in a polymer phase consisting of polymer dissolved in a volatile organic solvent such as methylene chloride. The suspension is then spray dried to produce polymer particles with entrapped treatment agent. The particle size is selected as described above with reference to solvent evaporation.

4. Cryogenic Process:

In this method, the treatment agent formulated as lyophilized powder is suspended in a polymer phase consisting of polymer dissolved in a volatile organic solvent such as methylene chloride. The suspension is sprayed into a container containing frozen ethanol overlaid with liquid nitrogen. The system is then warmed to −70° C. to liquify the ethanol and extract the organic solvent from the treatment agent particles. The hardened microspheres are collected by filtration or centrifugation and lyophilized.

5. Electrospraying:

In this method, a solution including a treatment agent, a biodegradable polymer and a solvent is formed. The solution is passed through an electrocharged nozzle and onto a collection assembly. A grounded electrode is positioned proximal to the collection assembly and used to attract the electrocharged solution to the collection assembly. The solvent then evaporates from the particulate solution to form particles having the treatment agent encapsulated within. The method described herein is similar in certain respects to the methods described in commonly-owned, co-pending, U.S. patent application Ser. No. 11/485,934 filed on Jul. 12, 2006 of Basu et. al. titled Methods and Devices for Forming Treatment Agent Carriers, incorporated herein by reference.

6. Example of Loading and Dose for Inhibiting Reperfusion Injury

As noted above, one example of the preparation of nanoparticles (e.g., nanospheres) or microparticles (e.g., microspheres) suitable for use in therapeutic angiogenesis is in the form of a solution. The solution may include any amount of the treatment agent found to inhibit or otherwise reduce reperfusion injury at a desired treatment site. Representatively, an immunosuppressant may make up between zero percent and 100 percent of the solution by volume. Still further, where the solution includes an antioxidant, the antioxidant may be between zero percent and 100 percent of the solution by volume. Alternatively, the solution may include a combination of an immunosuppressant, an antioxidant and/or a drug, wherein each component is included in the solution at an amount found to inhibit or otherwise reduce reperfusion injury at a desired treatment site.

Nanoparticles or microparticles may be loaded with a desired treatment agent in the range of about 0.5 to about 30 percent w/v. In the case of immunosuppressant agents, loading may be as high as 100 percent w/v. Representatively, in a 0.2 ml solution five percent w/v of particles provides for maximal dose of 10 micrograms of material per injection.

The number of injections is determined by an operator. The total dose is in the range of about 1 microgram to about 1 gram. It is to be appreciated that the optimal dose may be determined in a relevant animal model of ischemia by delivering the nanoparticles and/or microparticle suspension through a needle catheter or simply by injecting during open-heart procedure and generating a dose-response curve.

7. Enhancing Retention of the Treatment Agent at a Treatment Site

In one embodiment, a surface of the carrier may be modified to enhance retention of the treatment agent at the desired region. For example, the carrier may be modified at the surface, by linker molecules having an affinity to the surface of the desired treatment region. For example, a molecule having an antibody, where the antibody has affinity to a receptor on a cell surface may be used to enhance retention of the treatment agent. In one embodiment, the molecule may have an antibody to CD-31 or CD-34, platelet/endothelial cell adhesion molecule (PECAM), intercellular adhesion molecule (ICAM), E-Selectin, von Willebrand factor (vWF) or other molecules expressed on the surface of endothelial cells.

In other embodiments, the carrier may be charged for enhanced capillary retention. Endothelial cells lining blood vessel membranes provide an anionic barrier between the circulating blood and body tissues. Studies of the permeability of the aorta endothelium in rats have shown that cationized macromolecules may be rapidly transported through the endothelium. It is therefore believed that adding a positive charge to the treatment agents will result in better retention of the agent within the vessel than where the agent is uncharged or negatively charged. In this aspect, a carrier encapsulating the treatment agent may be modified by any standard method suitable for providing the carrier surface with a positive charge. In one embodiment, positively charged microspheres may be made by coating microparticles with Chitosan. Alternatively, positively charged microspheres may be made, for example, entirely of Chitosan in a water-in-oil emulsion process and crosslinked with glutaraldehye or genipin. In this aspect, the treatment agent may be swell loaded in the crosslinked spheres. Still further, if the treatment agent is soluble at pH 5, the treatment agent may be incorporated into the initial Chitosan solution, provided it does not subsequently react with the aldehyde crosslinker. Another approach for forming cationic microspheres may include using a poly-lysine graft of poly-lactic-co-glycolic acid (PLGA).

In still further embodiments, enhanced capillary retention of the treatment agent may be achieved by modifying a particle size of the treatment agent. Treatment agents, including treatment agents combined with a carrier (e.g., a sustained release carrier), having a particle size greater than about ten microns (μm) have the potential, when introduced into the arterial vascular system, of being trapped in the capillary bed. In this aspect, the carrier size is modified so that it is small enough to travel through a vessel lumen however large enough such that it will become lodged within, for example, a capillary vessel where treatment is desired. In some embodiments, the average diameter of the carrier may be about 10 μm or less. In other embodiments, the carrier may have an average diameter between approximately 5 μm and 10 μm. In still further embodiments, the carrier may have an average diameter of between approximately 7 μm and 10 μm. In other embodiment where it is not necessary for the treatment agent to travel through a vessel lumen (e.g. a peri-adventitial treatment site) the average diameter of the carrier may be approximately 100 μm or less.

One concern of introducing treatment agents and/or compositions into blood vessels or the myocardium is that the compositions remain (at least partially) at the treatment site for the desired treatment duration. Accordingly, in another embodiment, a delivery device (e.g. a catheter assembly) is described for accurately locating a treatment agent at a location in a blood vessel. It is appreciated that a catheter assembly is one technique for introducing treatment agents and the following description is not intended to limit the application or placement of the treatment agent compositions described above.

In one aspect, reperfusion injury may be inhibited by delivering a treatment agent to a reperfused vessel region distal to the obstructed region. Alternatively, reperfusion injury may be inhibited by delivering a treatment agent to an unperfused vessel region distal to the obstructed region.

For example, in reference to FIG. 2, treatment agents may be placed at region 210 prior to or during recanalization of the vessel region constricted by occlusion 204. Suitable sustained-release carriers encapsulating the treatment agent may take the form of polymer nanoparticles or microparticles, typically in the form of nanospheres or microspheres.

FIGS. 4-7 illustrate various embodiment of a delivery device. In general, the delivery device provides a system for delivering a substance, such as a treatment agent or a combination of treatment agents optionally presented as a sustained release composition, to or through a desired area of a blood vessel (a physiological lumen) or tissue in order to treat a localized area of the blood vessel. The delivery devices include a catheter assembly, which is intended to broadly include any medical device designed for insertion into a blood vessel or physiological lumen to permit injection and/or withdrawal of fluids, to maintain the potency of the lumen, or for any other purpose.

Figure 4:
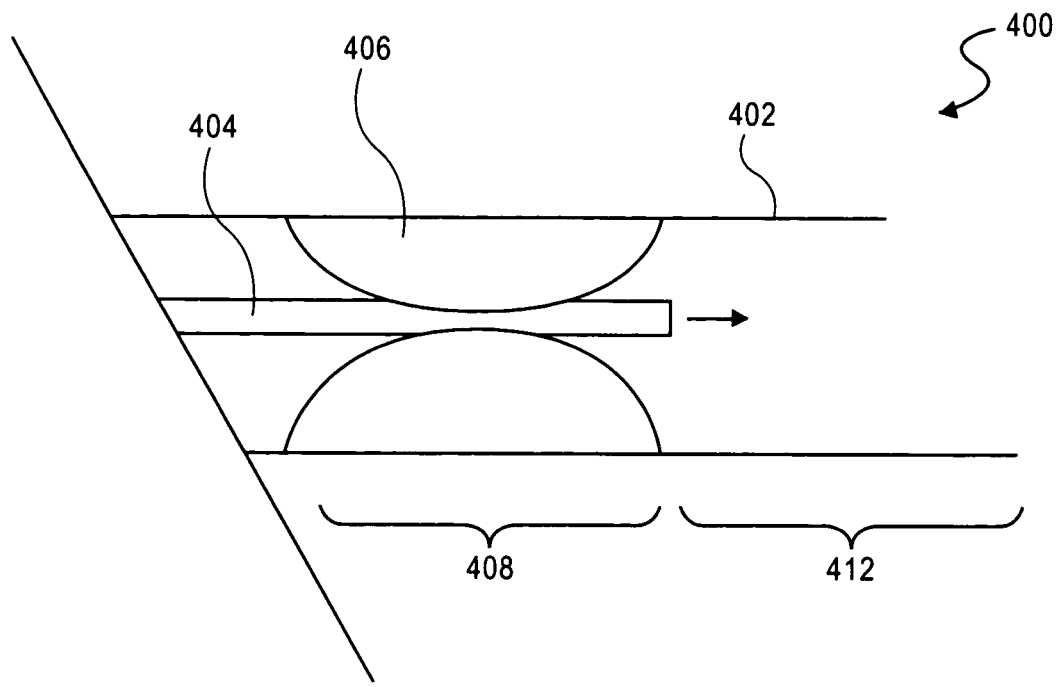
FIG. 4 shows a cross-sectional view of a first embodiment of a delivery device in the form of a catheter assembly in an occluded blood vessel.
Figure 4:
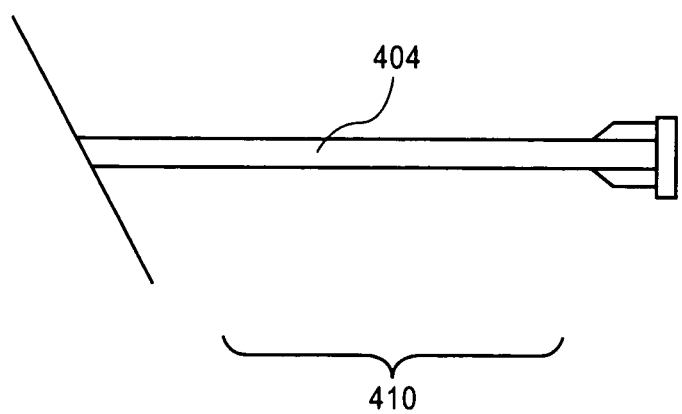

Referring to FIG. 4, a cross-sectional view of a first embodiment of a delivery device in the form of a catheter assembly in an occluded blood vessel is shown. In this embodiment, catheter assembly 400 is shown as a single guidewire catheter within a blood vessel lumen 402. Catheter assembly 400 includes proximal portion 410 and distal portion 408. Proximal portion 410 may be external to blood vessel 402 and to the patient. Representatively, catheter assembly 400 may be inserted through a femoral artery and through, for example, a guide catheter and with the aid of a guidewire to a location in the vasculature of a patient. That location may be, for example, a coronary artery. FIG. 4 shows distal portion 408 of catheter assembly 400 positioned adjacent occlusion 406 and proximal or upstream from treatment region 412. In other embodiments, a retrograde approach may be used to deliver a treatment agent. According to this approach, distal portion 408 of catheter assembly 400 is positioned distal or downstream from occlusion 406 and either distal to or within treatment region 412 such that a treatment agent may be released from catheter assembly 400 in a direction opposite that of the direction of blood flow. Returning to the embodiment illustrated in FIG. 4, guidewire cannula 404 is shown extending from a proximal end 410 to a distal end 408 of catheter assembly 400. A guidewire (shown at this point within guidewire cannula 404) allows for guidewire cannula 404 to be fed and maneuvered to a desired region within blood vessel 402.

FIG. 4 illustrates an embodiment where the vessel is almost completely obstructed by occlusion 406. In this aspect, blood flow to a region 412 distal to occlusion 406 may be completely blocked by occlusion 406. In this embodiment, the desired treatment region 412 may be an unperfused region 412 distal to occlusion 406. Alternatively, where occlusion 406 reduces blood flow into distal vessel regions without completely stopping the flow, region 412 may be a partially perfused region distal to occlusion 406. Returning to the embodiment where substantially all of the vessel lumen is occluded, guidewire cannula 404 may be of a diameter that allows for guidewire cannula 404 to be advanced through occlusion 406 without disrupting the occlusion to region 412. In this aspect, guidewire cannula 404 may have a diameter of approximately 0.02 inches or less. Since occlusion 406 is not disrupted, blood flow has not been reintroduced to region 412 therefore cell damage due to the inflammatory and oxidative effects associated with reintroducing blood flow to ischemic region 412 (i.e. reperfusion injury) has not yet begun. Once in position, the guidewire may be removed from guidewire cannula 404 to allow for delivery of a treatment agent through the lumen of guidewire cannula 404 to pretreat region 412.

After delivery of the treatment agent, a device suitable for recanalizing the occluded region (e.g. a balloon) may be advanced through the vessel lumen and positioned within the occluded region. In one embodiment, the device may be advanced over guidewire cannula 404 already in place. Alternatively, guidewire cannula 404 may be removed and a separate guidewire assembly may be maneuvered to the occluded region and the device advanced over the separate guidewire assembly. In some embodiments, the device may be a balloon angioplasty catheter advanced over the guidewire. Alternatively, the device may be a stent delivery catheter. Once in position, the device may be used to recanalize the vessel lumen thereby allowing blood flow to return to pretreated region 412.

Figure 5:
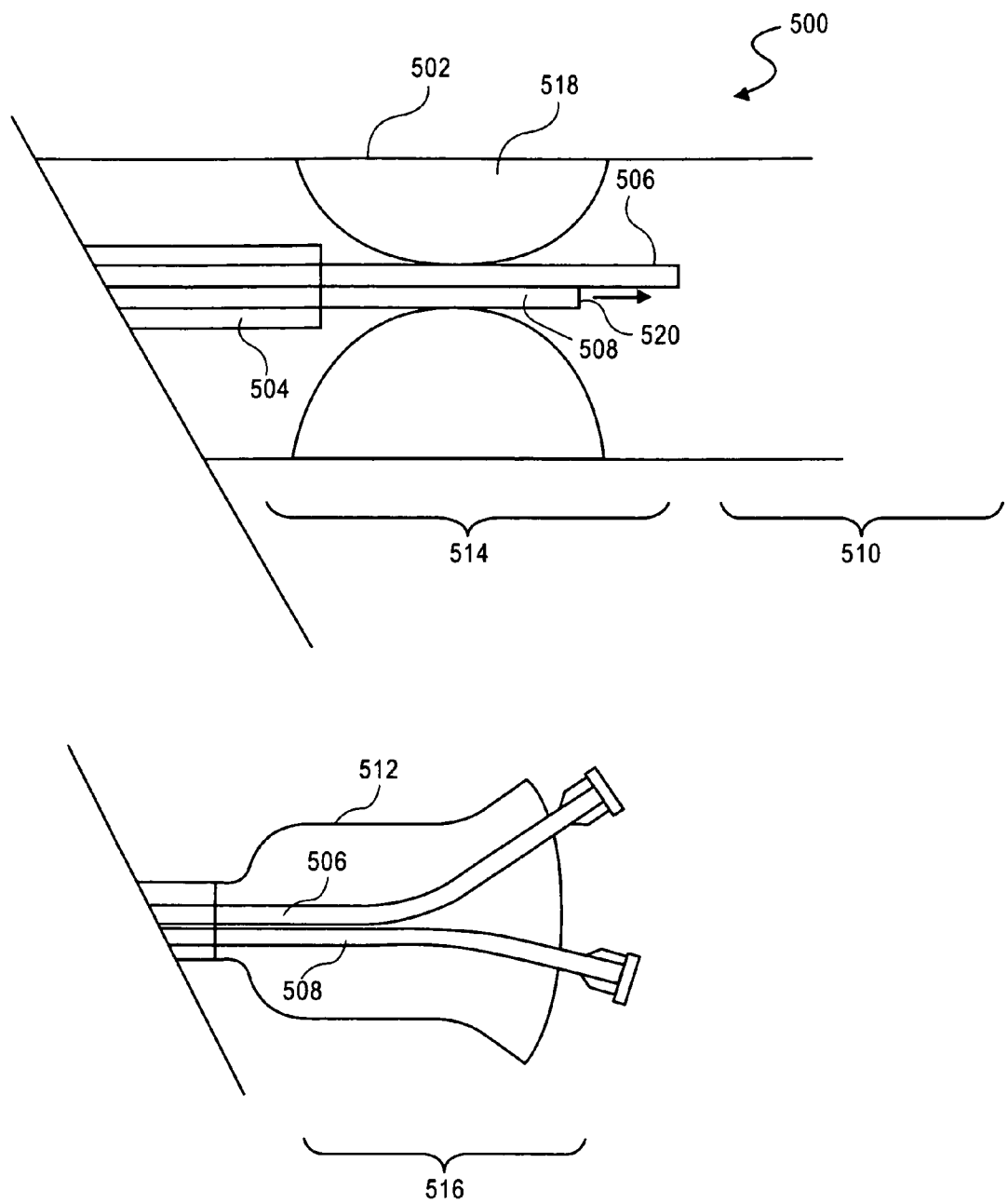
FIG. 5 shows a cross-sectional view of a second embodiment of a delivery device in the form of a catheter assembly in an occluded vessel.

Referring to FIG. 5, a cross-sectional view of a second embodiment of a delivery device in the form of a catheter assembly in an occluded vessel is shown. Catheter assembly 500 is shown positioned within a lumen of blood vessel 502 adjacent occlusion 518. Catheter assembly 500 includes proximal portion 516 and distal portion 514. Proximal portion 516 may be external to blood vessel 502 and to the patient. Representatively, catheter assembly 500 may be inserted through a femoral artery and through, for example, a guide catheter and with the aid of a guidewire to a location in the vasculature of a patient. That location may be, for example, a coronary artery. FIG. 5 shows distal portion 514 of catheter assembly 500 positioned adjacent occlusion 518 and upstream a treatment region 510. In other embodiments, a venous access retrograde approach may be used to deliver a treatment agent. According to this approach, the catheter enters the venous tree through the coronary sinus. A balloon is inflated to occlude the vessel and the treatment suspension is pressure perfused into the tissue in a direction opposite the direction of natural blood flow.

In one embodiment, catheter assembly 500 includes primary cannula 504 having a length that extends from proximal portion 516 (e.g., located external through a patient during a procedure) to distal portion 514. Primary cannula 504 has a lumen there through that includes a guidewire cannula 506 and delivery cannula 508. Each of guidewire cannula 506 and delivery cannula 508 extends from proximal portion 516 of catheter assembly 500 to distal portion 514. A guidewire (shown at this point within guidewire cannula 506) allows for guidewire cannula 506 to be fed and maneuvered to a desired region within blood vessel 502. Delivery cannula 508 allows for delivery of a treatment agent to a desired vessel region. A proximal end of guidewire cannula 506 and delivery cannula 508 are confined within a hub 512 located outside of the patient's body.

A delivery port 520 of delivery cannula 508 may be positioned within a treatment region 510 distal to occlusion 518 and upstream from treatment region 510. Once in position, the treatment agent may be delivered through delivery cannula 508 to delivery port 520 for infusion of the treatment agent within region 510. In this aspect, delivery of the treatment agent is localized to region 510 susceptible to reperfusion injury.

Figure 6:
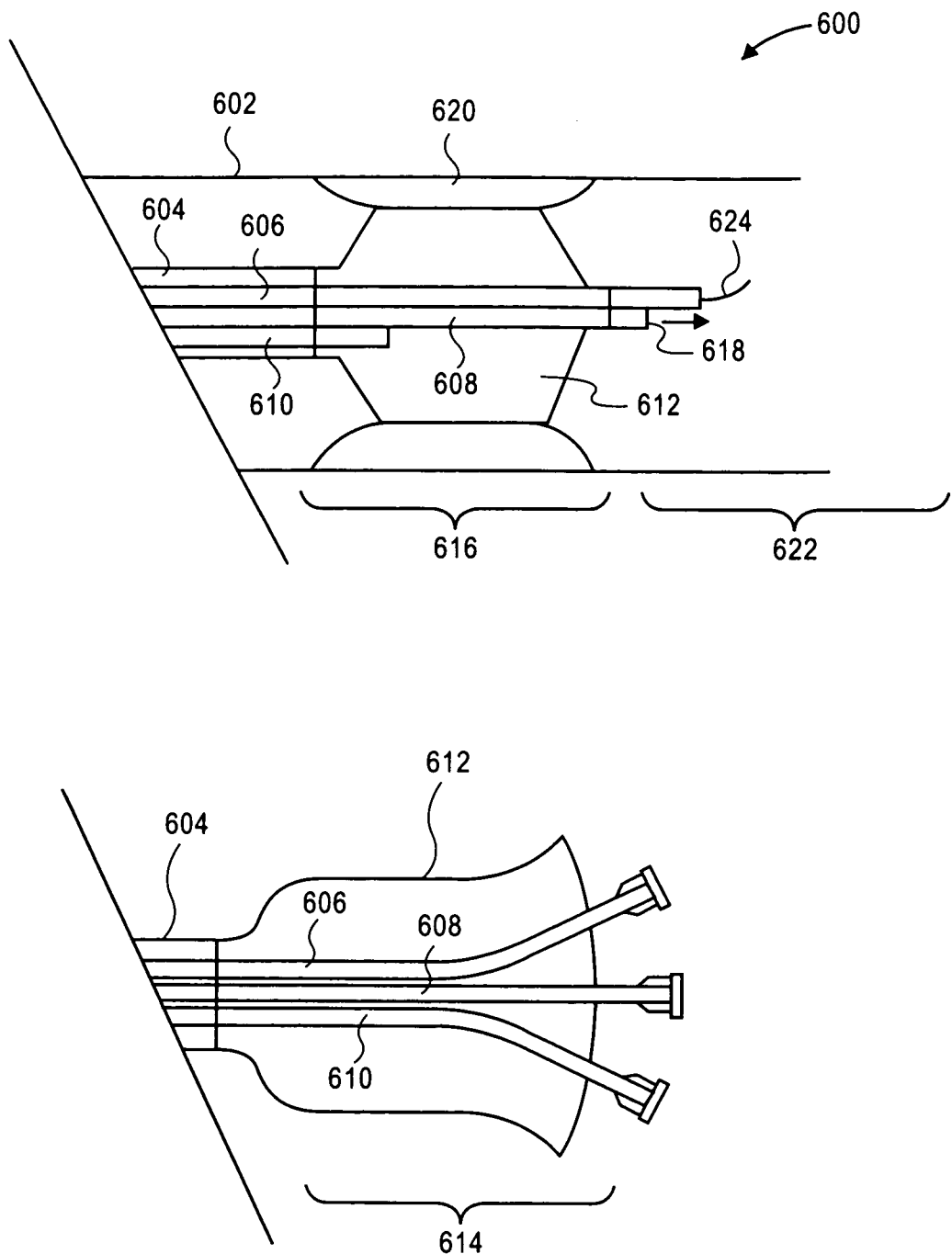
FIG. 6 shows a cross-sectional view of a third embodiment of a delivery device in the form of a catheter assembly in an occluded vessel.

FIG. 6 shows a cross-sectional view of a third embodiment of a delivery device in the form of a catheter assembly in an occluded vessel. Catheter assembly 600 is shown disposed within blood vessel 602. Catheter assembly 600 includes proximal portion 614 and distal portion 616. Proximal portion 614 may be external to blood vessel 602 and to the patient. Representatively, catheter assembly 600 may be inserted through a femoral artery and through, for example, a guide catheter and with the aid of a guidewire to a location in the vasculature of a patient. That location may be, for example, a coronary artery. FIG. 6 shows distal portion 616 of catheter assembly 600 positioned adjacent occlusion 620 and upstream a treatment region 622. In other embodiments, a venous access retrograde approach may be used to deliver a treatment agent. According to this approach, the catheter enters the venous tree through the coronary sinus. A balloon is inflated to occlude the vessel and the treatment suspension is pressure perfused into the tissue in a direction opposite the direction of natural blood flow.

In one embodiment, catheter assembly 600 includes primary cannula 604 having a length that extends from proximal portion 614 (e.g., located external through a patient during a procedure) to connect with a proximal end or skirt of balloon 612. Primary cannula 604 has a lumen there through that includes guidewire cannula 606, inflation cannula 610 and delivery cannula 608. Each of guidewire cannula 606, inflation cannula 610 and delivery cannula 608 extends from proximal portion 614 of catheter assembly 600 to distal portion 616. Inflation cannula 610 has a distal end that terminates within balloon 612. Guidewire cannula 606 and delivery cannula 608 extend through balloon 612.

Guidewire cannula 614 has a lumen sized to accommodate guidewire 624. Catheter assembly 600 may be an over the wire (OTW) configuration where guidewire cannula 606 extends from a proximal end (external to a patient during a procedure) to a distal end of catheter assembly 600. Guidewire cannula 606 may also be used for delivery of a treatment agent such as an immunosuppressant or antioxidant when guidewire 624 is removed with catheter assembly 600 in place. In such case, separate delivery cannula (i.e., delivery cannula 608) is unnecessary or a delivery cannula may be used to deliver one treatment agent while guidewire cannula 606 is used to delivery another treatment agent.

In another embodiment, catheter assembly 600 is a rapid exchange (RX) type catheter assembly and only a portion of catheter assembly 600 (a distal portion including balloon 612) is advanced over guidewire 624. In an RX type of catheter assembly, typically, the guidewire cannula/lumen extends from the distal end of the catheter to a proximal guidewire port spaced distally from the proximal end of the catheter assembly. The proximal guidewire port is typically spaced a substantial distance from the proximal end of the catheter assembly.

In one embodiment, catheter assembly 600 is introduced into blood vessel 620 and balloon 612 is inflated (e.g., with a suitable liquid through inflation cannula 610) to recanalize the blood vessel. Prior to or during recanalization, a solution (fluid) including a treatment agent is introduced through delivery cannula 608 through delivery port 618. The treatment agent may be a solution of an immunosuppresant, an antioxidant and/or a drug. By introducing the treatment agent in this manner, the treatment agent can inhibit cellular responses leading to reperfusion injury within region 622 prior to (e.g. pretreat) or while blood is reintroduced to the ischemic region 622.

Figure 7:
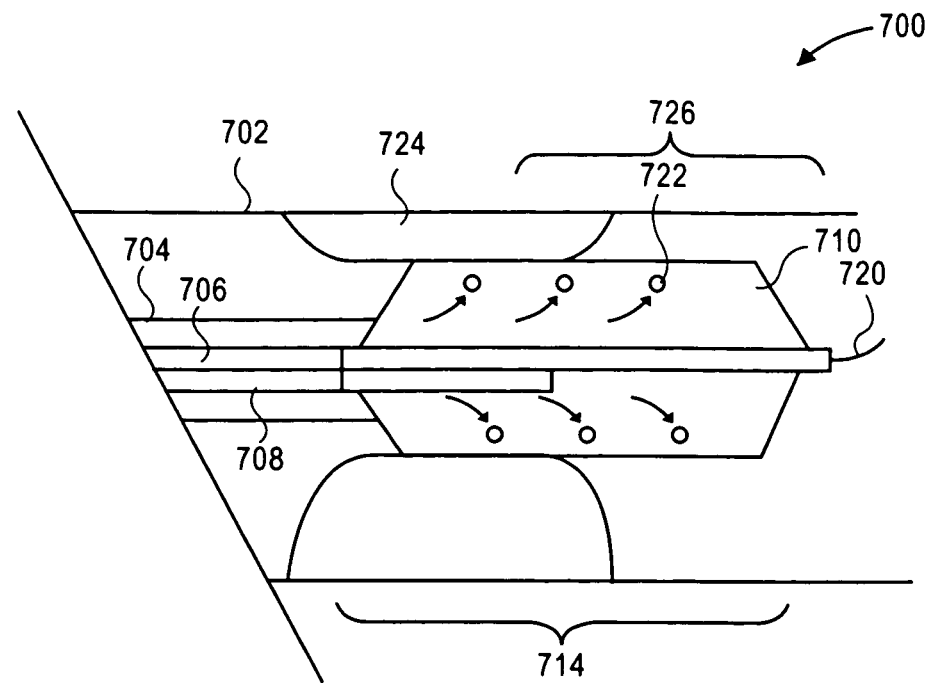
FIG. 7 shows a cross-sectional view of a fourth embodiment of a delivery device in the form of a catheter assembly in an occluded vessel.
Figure 7:
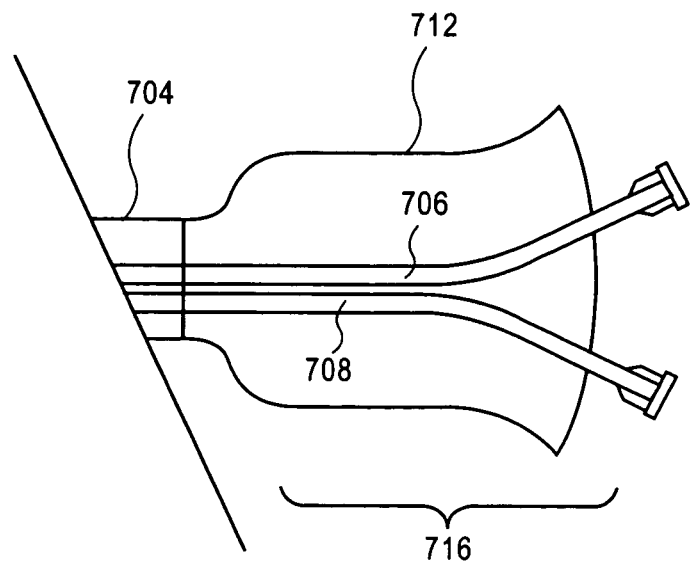

FIG. 7 shows a cross-sectional view of a fifth embodiment of a delivery device in the form of a catheter assembly in an occluded vessel. FIG. 7 shows catheter assembly 700 disposed within blood vessel 702. Catheter assembly 700 includes primary cannula 704 having a length that extends from a proximal end of catheter assembly 700 (e.g., located external to a patient during a procedure) to connect with a proximal and/or skirt of balloon 710. Balloon 710, in this embodiment, is located at a position aligned with a treatment region 726 distal to occlusion 724 in blood vessel 702. Representatively, catheter assembly 700 may be inserted through a femoral artery and through, for example, a guide catheter and with the aid of a guidewire to a location in the vasculature of a patient. That location may be, for example, a coronary artery.

Disposed within primary cannula 704 is guidewire cannula 706 and inflation cannula 708. Guidewire cannula 706 extends from a proximal end 716 of catheter assembly 700 through balloon 710. A distal end or skirt of balloon 710 is connected to a distal portion of guidewire cannula 706.

Inflation cannula 708 extends from a proximal end 716 of catheter assembly 700 to a point within balloon 710. In one embodiment, balloon 710 is made of a porous material such as expanded polytetrafluoroethylene (ePTFE). A suitable pore size for an ePTFE balloon material is on the order of 1 μm to 60 μm. The porosity of ePTFE material can be controlled to accommodate a treatment agent flow rate or particle size by changing a microstructure of an ePTFE tape used to form a balloon, for example, by wrapping around a mandrel. Alternatively, pore size may be controlled by controlling the compaction process of the balloon, or by creating pores (e.g., micropores) using a laser.

ePTFE as a balloon material is a relatively soft material and tends to be more flexible and conformable with tortuous coronary vessels than conventional balloons. ePTFE also does not need to be folded which will lower its profile and allow for smooth deliverability to distal lesions and the ability to provide therapy to targeted or regional sites post angioplasty and/or stent deployment.

A size of balloon 710 may also vary. A suitable balloon diameter is, for example, in the range of two to five millimeters (mm). A balloon length may be on the order of about 8 mm to about 60 mm. A suitable balloon profile range is, for example, about 0.030 inches to about 0.040 inches.

In one embodiment, catheter assembly 700 is inserted into blood vessel 702 so that balloon 710 is aligned with treatment region 726. Following alignment of balloon 710 of catheter assembly 700, balloon 710 may be inflated by introducing a formulation of the treatment agent (e.g., treatment agent through inflation cannula 708). In one embodiment, balloon 710 is only partially inflated or has an inflated diameter less than an inner diameter of blood vessel 702 at treatment region 726. In this manner, balloon 710 does not contact or only minimally contacts the blood vessel wall. A suitable expanded diameter of balloon 710 is on the order of 2 mm to 5 mm for coronary vessels. The treatment agent flows through inflation cannula 708 and then permeates through the pores 722 within balloon 710 into blood vessel 702 at the treatment region 726.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A method comprising:
   introducing a catheter assembly to an obstructed region of a blood vessel lumen, the catheter assembly comprising a primary cannula, a fluid delivery cannula and a guidewire cannula, the fluid delivery cannula and the guidewire cannula being separate cannulas positioned within, and extending from a proximal end to a distal end of, the primary cannula, the guidewire cannula having an outer surface positioned along, and interfacing with, an outer surface of the fluid delivery cannula such that they are side by side within the primary cannula, each of the fluid delivery cannula and the guidewire cannula having a distal end and a proximal end, wherein the distal ends of the fluid delivery cannula and the guidewire cannula are advanced through the obstructed region, and wherein the distal end of the guidewire cannula is open to the blood vessel lumen such that a guidewire advanced through the guidewire cannula and out the distal end is exposed to the blood vessel lumen, and the distal end of the fluid delivery cannula comprises a single fluid delivery port, and the single fluid delivery port is positioned distal to the distal end of the primary cannula and within a region of the blood vessel lumen downstream to the obstructed region while the proximal end of the fluid delivery cannula and the guidewire cannula are positioned external to the blood vessel;
   recanalizing the obstructed region with the catheter assembly; and
   during recanalization, delivering a treatment agent through the fluid delivery port and into the region of the blood vessel lumen downstream to the obstructed region, the treatment agent having a property that will inhibit reperfusion injury, and the treatment agent comprises at least one of an immunosuppressant or an antioxidant.

2. The method of claim 1, wherein introducing comprises positioning the catheter assembly in a coronary sinus and delivering comprises releasing the treatment agent from the catheter assembly.

3. The method of claim 1, wherein the catheter assembly is an angioplasty catheter.

4. The method of claim 1, wherein the immunosuppressant is selected from the group consisting of corticosteroids, everolimus, rapamycin and derivatives thereof.

5. The method of claim 1, wherein the antioxidant is selected from the group consisting of ascorbic acid, proanthocyanadins, carotenoids, tocopherol, selenium, N-acetylcarnitine, R-lipoic acid and coenzyme Q-10.

6. The method of claim 1, wherein the treatment agent further comprises a drug selected from the group consisting of cariporide, eniporide, zoniporide, nicaraven, MLN01, nicorandil, raloxifene, edaravone, adenosine and carvedilol.

7. The method of claim 6, wherein 100 percent of the drug is released over a 72 hour period.

8. The method of claim 1, wherein the treatment agent is disposed in a sustained release carrier.

9. The method of claim 8, wherein the carrier comprises particles having an average diameter on the order of 10 microns (μm) or less.

10. The method of claim 1, wherein the treatment agent is disposed in a carrier having an agent directed to a specific binding site on an endothelial cell.

11. The method of claim 1, wherein the treatment agent is disposed in a charged carrier for enhanced capillary retention.

12. A method comprising:
introducing a medical device having a porous balloon to an obstructed region of a blood vessel lumen by advancing a distal end of the porous balloon through the obstructed region and into a region within the blood vessel lumen downstream of the obstructed region;
recanalizing the obstructed region with the medical device; and
delivering a treatment agent through the porous balloon to the region within the blood vessel lumen downstream of the obstructed region prior to reperfusion of the region within the blood vessel lumen downstream of the obstructed region, the treatment agent comprising at least one of an immunosuppressant and an antioxidant, wherein during delivering, the porous balloon is only partially inflated to a diameter less than an inner diameter of the blood vessel lumen at the obstructed region such that, during delivery, an obstruction remains within the obstructed region and the porous balloon does not contact a blood vessel wall defining the lumen.

13. The method of claim 12, wherein introducing comprises positioning the medical device in a coronary sinus and delivering comprises infusion of the treatment agent.

14. The method of claim 12, wherein the medical device is one of an angioplasty catheter and a stent delivery catheter.

15. The method of claim 12, wherein the immunosuppressant is selected from the group consisting of corticosteroids, everolimus, rapamycin and derivatives thereof.

16. The method of claim 12, wherein the antioxidant is selected from the group consisting of ascorbic acid, proanthocyanadins, carotenoids, tocopherol, selenium, N-acetyl-carnitine, R-lipoic acid and coenzyme Q-10.

17. The method of claim 12, wherein the treatment agent is a drug selected from the group consisting of cariporide, eniporide, zoniporide, nicaraven, MLN01, nicorandil, raloxifene, edaravone, adenosine and carvedilol.

18. The method of claim 12, wherein the treatment agent is disposed in a sustained release carrier.

19. The method of claim 18, wherein 100 percent of the drug is released over a 72 hour period.

20. The method of claim 18, wherein the carrier comprises particles having an average diameter on the order of 10 microns (μm) or less.

21. The method of claim 12, wherein the treatment agent is disposed in a carrier having an agent directed to a specific binding site on an endothelial cell.

22. The method of claim 12, wherein the treatment agent is disposed in a charged carrier for enhanced capillary retention.

23. A method comprising:
introducing a primary cannula, a fluid delivery cannula and a guidewire cannula to an unperfused region of an occluded vessel lumen which is downstream from the occlusion without occluding blood flow upstream to the occlusion, the guidewire cannula and the fluid delivery cannula being separate cannulas positioned within the primary cannula, the guidewire cannula having an outer surface positioned along, and interfacing with, an outer surface of the fluid delivery cannula, and each of the fluid delivery cannula and the guidewire cannula having a distal portion and a proximal portion defining a length dimension of the cannulas that extends from a distal end to a proximal end of the primary cannula, wherein an end of the distal portion of the guidewire cannula is open to the blood vessel lumen such that a guidewire advanced through the guidewire cannula and out the end of the distal portion is exposed to the blood vessel lumen, and wherein introducing comprises advancing the distal portion of each of the fluid delivery cannula and the guidewire cannula through the occlusion and to the unperfused region, wherein advancing the distal portion does not disrupt the occlusion in a manner that causes blood to be reintroduced to the unperfused region, and wherein the proximal portion of each of the fluid delivery cannula and the guidewire cannula is external to the vessel;
delivering a treatment agent having a property that will inhibit reperfusion injury through the fluid delivery cannula to the unperfused region, and the treatment agent comprises at least one of an immunosuppressant or an antioxidant; and
after delivering the treatment agent, recanalizing the occluded vessel by advancing an angioplasty device into the occluded vessel to restore blood flow to the unperfused region.

24. The method of claim 23, wherein a balloon of the angioplasty device is advanced over the delivery cannula.

25. The method of claim 23, wherein the delivery cannula is removed prior to recanalizing the occluded vessel.

26. The method of claim 23, wherein the immunosuppressant is selected from the group consisting of corticosteroids, everolimus, rapamycin or derivatives thereof.

27. The method of claim 23, wherein the antioxidant is selected from the group consisting of ascorbic acid, proanthocyanadins, carotenoids, tocopherol, selenium, N-acetyl-carnitine, R-lipoic acid and coenzyme Q-10.

28. The method of claim 27, wherein the carrier comprises particles having an average diameter on the order of 10 microns (μm) or less.

29. The method of claim 23, wherein the treatment agent further comprises a drug selected from the group consisting of cariporide, eniporide, zoniporide, nicaraven, MLN01, nicorandil, raloxifene, edaravone, adenosine and carvedilol.

30. The method of claim 29, wherein 100 percent of the drug is released over a 72 hour period.

31. The method of claim 23, wherein the treatment agent is disposed in a sustained release carrier.

32. The method of claim 23, wherein the treatment agent is disposed in a carrier having an agent directed to a specific binding site on an endothelial cell.

33. The method of claim 23, wherein the treatment agent is disposed in a charged carrier for enhanced capillary retention.

34. The method of claim 23, wherein the delivery cannula comprises a diameter of 0.02 inches or less.

* * * * *